United States Patent
Ikushima (10) Patent No.: US 12,036,574 B2
(45) Date of Patent: Jul. 16, 2024

(54) LIQUID MATERIAL DISCHARGE DEVICE FOR DISCHARGING A FIXED AMOUNT OF LIQUID MATERIAL

(71) Applicant: MUSASHI ENGINEERING, INC., Mitaka (JP)

(72) Inventor: Kazumasa Ikushima, Tokyo (JP)

(73) Assignee: MUSASHI ENGINEERING, INC., Mitaka (JP)

( * ) Notice: Subject to any disclaimer, the term of this patent is extended or adjusted under 35 U.S.C. 154(b) by 248 days.

(21) Appl. No.: 15/745,779

(22) PCT Filed: Jul. 21, 2016

(86) PCT No.: PCT/JP2016/071340
§ 371 (c)(1),
(2) Date: Jan. 18, 2018

(87) PCT Pub. No.: WO2017/018303
PCT Pub. Date: Feb. 2, 2017

(65) Prior Publication Data
US 2018/0208390 A1    Jul. 26, 2018

(30) Foreign Application Priority Data

Jul. 24, 2015 (JP) ................................ 2015-146451

(51) Int. Cl.
B05C 17/01 (2006.01)
B05C 5/00 (2006.01)
(Continued)

(52) U.S. Cl.
CPC ............ B05C 11/1013 (2013.01); B05C 5/00 (2013.01); B05C 5/0225 (2013.01); B05C 11/10 (2013.01);
(Continued)

(58) Field of Classification Search
CPC . B05C 5/0225; B05C 17/015; B05C 17/0126; B05C 11/1034; A61B 17/00491;
(Continued)

(56) References Cited

U.S. PATENT DOCUMENTS 2,246,594 A * 6/1941 Kinsella ............... G05D 7/0166
222/1
3,057,517 A * 10/1962 Douglas ............... B67D 1/0462
222/1
(Continued)

FOREIGN PATENT DOCUMENTS

JP        9-85151 A      3/1997
JP     2007-152165 A    6/2007
(Continued)

OTHER PUBLICATIONS

Office Action of Korean application No. 10-2018-7001454 issued on Aug. 25, 2022 with English translation.
(Continued)

*Primary Examiner* — Karl Kurple
(74) *Attorney, Agent, or Firm* — WHDA, LLP (57) ABSTRACT

A discharge device capable of suppressing pressure fluctuation of a compressed gas supplied to a container in which a liquid material is stored. The device includes a storage container in which a liquid material is stored; a discharge port through which the liquid material is discharged; a pressure control valve that adjusts a pressure of a compressed gas supplied from an external compressed gas source to a desired level; a discharge valve that establishes or cuts off communication between the pressure control valve and the storage container; a control device that controls operation of the discharge valve; a first flow line connecting the pressure control valve and the discharge valve; and a second flow line connecting the discharge valve and the storage container. The device further includes a third
(Continued)

flow line branched from the first flow line, and a leak mechanism connected to the third flow line.

14 Claims, 9 Drawing Sheets

(51) Int. Cl.
| | |
|---|---|
| *B05C 5/02* | (2006.01) |
| *B05C 11/10* | (2006.01) |
| *B05C 17/005* | (2006.01) |
| *B65D 83/66* | (2006.01) |
| *A61B 17/00* | (2006.01) |
| *G05D 16/02* | (2006.01) |

(52) U.S. Cl.
CPC .. *B05C 17/00573* (2013.01); *B05C 17/00593* (2013.01); *B05C 17/014* (2013.01); *B65D 83/66* (2013.01); *A61B 17/00491* (2013.01); *G05D 16/02* (2013.01)

(58) Field of Classification Search
CPC ............. Y10T 137/7782; G01F 11/021; G01F 11/023; G01F 11/029
USPC ............ 222/61, 71, 135, 394–397, 256–263; 137/489.5, 14
See application file for complete search history.

(56) References Cited

U.S. PATENT DOCUMENTS

| | | | | | |
|---|---|---|---|---|---|
| 3,250,293 | A | * | 5/1966 | Adams | G05D 7/0635 251/129.08 |
| 3,933,285 | A | * | 1/1976 | Wiggins | B05B 5/1616 222/56 |
| 4,346,732 | A | * | 8/1982 | Moos | B05B 12/087 137/489 |
| 4,634,027 | A | * | 1/1987 | Kanarvogel | B05C 17/002 137/541 |
| 4,759,477 | A | * | 7/1988 | Gelinas | B05C 5/0225 222/504 |
| 5,016,665 | A | * | 5/1991 | Konieczynski | B05B 12/004 137/489.5 |
| 5,029,731 | A | * | 7/1991 | Klatt | G01F 11/029 118/694 |
| 5,031,805 | A | * | 7/1991 | Rohmann | B22D 39/06 222/590 |
| 5,188,258 | A | * | 2/1993 | Iwashita | B05C 11/1013 222/61 |
| 5,226,575 | A | * | 7/1993 | Faust | E04F 21/12 222/397 |
| 5,277,333 | A | * | 1/1994 | Shimano | G05D 7/0658 222/14 |
| 5,332,125 | A | * | 7/1994 | Schmitkons | B01F 15/00175 222/1 |
| 5,474,214 | A | * | 12/1995 | Chung | F16N 5/02 222/262 |
| 5,707,013 | A | * | 1/1998 | Konieczynski | B05B 5/1625 239/69 |
| 5,863,146 | A | * | 1/1999 | Denkins | B05B 7/2437 401/171 |
| 6,016,937 | A | * | 1/2000 | Clay | B05C 17/00516 222/330 |
| 6,431,096 | B1 | * | 8/2002 | Engelke | A01C 23/028 222/61 |
| 6,669,051 | B1 | * | 12/2003 | Phallen | B67C 3/281 222/1 |
| 6,799,698 | B2 | * | 10/2004 | Ono | B05C 11/1047 222/386 |
| 7,121,287 | B2 | * | 10/2006 | Carhuff | B08B 9/0321 134/169 R |
| 7,527,768 | B2 | * | 5/2009 | Ikushima | B05C 11/1002 222/53 |
| 8,220,661 | B2 | * | 7/2012 | Ng | B05C 17/00573 222/397 |
| 8,251,261 | B2 | * | 8/2012 | Ikushima | B05C 5/02 137/884 |
| 8,608,025 | B2 | * | 12/2013 | MacIndoe | B05B 9/04 222/1 |
| 8,770,439 | B2 | | 7/2014 | Ikushima | |
| 2007/0068974 | A1 | * | 3/2007 | Tourigny | G01F 11/023 222/389 |
| 2007/0108225 | A1 | * | 5/2007 | O'Dougherty | B67D 7/0261 222/1 |
| 2008/0230492 | A1 | * | 9/2008 | Kao | G03F 7/162 210/791 |
| 2009/0120357 | A1 | * | 5/2009 | Ikushima | B05C 5/02 118/300 |
| 2010/0025428 | A1 | * | 2/2010 | Ng | B05C 17/00573 222/61 |
| 2010/0090137 | A1 | * | 4/2010 | Kato | G05D 7/0635 137/511 |
| 2010/0176161 | A1 | * | 7/2010 | Conner | B05C 5/0212 222/389 |
| 2012/0104033 | A1 | * | 5/2012 | MacIndoe | B05B 9/04 222/389 |
| 2012/0132671 | A1 | * | 5/2012 | Ikushima | B05C 11/1034 222/1 |
| 2013/0260569 | A1 | * | 10/2013 | Ganster | H01L 21/67017 438/745 |
| 2015/0028055 | A1 | * | 1/2015 | Hayama | B05C 5/025 222/55 |
| 2015/0155188 | A1 | * | 6/2015 | Jung | H01L 21/67034 216/59 |

FOREIGN PATENT DOCUMENTS

| | | | |
|---|---|---|---|
| JP | 2007152165 | A * | 6/2007 |
| JP | 5460132 | B2 | 4/2014 |
| KR | 10-2010-0040684 | A | 4/2010 |
| KR | 10-2013-0076581 | A | 7/2013 |

OTHER PUBLICATIONS

Office Action dated Jan. 9, 2023, issued in counterpart KR application No. 10-2022-7043836, with English translation. (12 pages).

* cited by examiner

LIQUID MATERIAL DISCHARGE DEVICE FOR DISCHARGING A FIXED AMOUNT OF LIQUID MATERIAL

TECHNICAL FIELD

The present invention relates to a discharge device for discharging a fixed amount of liquid material through a discharge port by supplying a compressed gas to a container in which the liquid material is stored.

BACKGROUND ART

The so-called air type dispenser is known which discharges a fixed amount of liquid material through a discharge port by supplying a compressed gas to a container in which the liquid material is stored. In order to realize discharge of the fixed amount of liquid material, it is important to control the compressed gas acting on the liquid material to be held under a constant pressure. In the air type dispenser, a pressure control valve, such as a regulator (pressure reducing valve) or a relief valve, is used for the above-mentioned control.

A known nozzle-flapper type regulator operates for pressure adjustment as follows. When a secondary-side air pressure rises above a setting value, a nozzle disposed in the inside is opened by part of the secondary-side air pressure that is returned to the inside through a feedback hole, whereupon a back pressure drops. With the dropping of the back pressure, a main valve is closed and a vent valve is opened. Thus, the compressed air under pressure having risen above the setting air pressure on the secondary side is vented to the atmosphere, and the air pressure is held at the setting value. As an example of a discharge device using the known nozzle-flapper type regulator, Patent Document 1 discloses a gas pulse discharge device comprising a gas supply source that supplies a gas under a pressure $P_0$, a discharge port, and a peak pressure generator that is connected to the gas supply source and the discharge port, wherein the peak pressure generator includes first pressure adjustment means and a first open-close valve connected to the discharge port side of the first pressure adjustment means, and operates to release the gas on the first pressure adjustment means side to the discharge port when the first open-close valve is opened, and wherein the first pressure adjustment means includes a first pressure reducing mechanism that reduces the pressure $P_0$ of the gas supplied from the gas supply source down to a pressure $P_1$, and a first pressure relief mechanism that is connected to the discharge port side of the first pressure reducing mechanism, and that vents, to the atmosphere, the gas on the discharge port side of the first pressure reducing mechanism when a pressure on the discharge port side of the first pressure reducing mechanism exceeds the pressure $P_1$.

A known relief valve operates for pressure adjustment as follows. When an air pressure in a pneumatic circuit exceeds a value set by an adjustment spring or by an externally-applied pilot pressure, a valve is opened to vent (relieve) air to the outside such that the air pressure in the pneumatic circuit is held at the setting value. As an example of a discharge device using the known relief valve, Patent Document 2 discloses a die-coater paint supply device comprising a paint container, a metering pump installed at a position lower than a liquid level in the paint container, a die coater, a first paint flow line extending from the inside of the paint container and connected to the suction side of the metering pump, and a second paint flow line connecting the discharge side of the metering pump and the die coater, the paint in the paint container being supplied to the die coater by the metering pump, wherein the paint container is constituted as a gastight container, a compressed gas supply system is connected to the paint container to pressurize the liquid level in the paint container by the compressed gas, and a relief valve is disposed at a fore end of a tube branched from the middle of the flow line.

While the compressed gas is supplied to the storage container through a discharge valve, there is a problem that, when the discharge valve is operated, an abrupt pressure drop generates in a flow passage communicating the storage container and the discharge valve with each other. Pressure fluctuation generated in that case can be suppressed to some extent by installing a buffer tank, which has a much larger volume than the storage container, in the flow passage communicating the storage container and the discharge valve with each other. However, such a solution is problematic in that the pressure fluctuation cannot be sufficiently suppressed unless the volume of the buffer tank is increased ten times or more, for example. In consideration of the above point, the applicant has proposed, in Patent Document 3, a method of discharging a fixed amount of liquid with which the pressure drop generated in the flow passage with the operation of the discharge valve is reduced by installing the buffer tank, and by setting a flow resistance in a flow passage downstream of the buffer tank to be larger than that in a flow passage upstream of the buffer tank.

CITATION LIST

Patent Documents

Patent Document 1: Japanese Patent Laid-Open Publication No. 2007-152165
Patent Document 2: Japanese Patent Laid-Open Publication No. H09-85151
Patent Document 3: Japanese Patent No. 5460132

SUMMARY OF INVENTION

Technical Problems

The above-described pressure control valve, such as the regulator (pressure reducing valve) or the relief valve, for controlling the pressure supplied from the compressed gas source to be held constant has the following problems.

In the regulator, for example, the secondary side pressure is adjusted by repeating a compressed-gas supply operation to raise the pressure and a compressed-gas relief operation to lower the pressure in a pressure oscillating manner during a period until the secondary side pressure is settled to the setting value. Such a setting pressure adjustment operation is not so problematic when the compressed gas is employed on the secondary side for a relatively long time. However, the pressure fluctuation affects a discharge amount when a discharge operation time for each shot is short as in the dispenser, or when discharge operations are successively performed at short intervals. In the air type dispenser, particularly, the influence of the pressure fluctuation may cause significant change (variation) in the discharge amount.

The above-described pressure fluctuation attributable to the setting pressure adjustment operation is more significant when a volume of components, such as the storage container (e.g., a syringe) and the flow lines (e.g., tubes), connected to the secondary side (the volume being called a "load capacity" hereinafter) is relatively small with respect to a flow rate of the compressed gas supplied from the regulator. This is because the operations of supplying and venting the compressed gas by the regulator provide an excessive load in comparison with the small load capacity.

The above-described pressure fluctuation appears, by way of example, as follows. (1) When the dispenser starts the discharge operation (when the discharge valve comes into a communication position), the compressed gas is caused to abruptly flow toward the storage container side (secondary side) from the regulator, Therefore, the pressure adjustment operation cannot keep up with the abrupt flow, and the secondary side pressure drops temporarily. (2) When the dispenser stops the discharge operation (when the discharge valve comes into a cutoff position), the compressed gas flowing from the regulator toward the storage container side (secondary side) is abruptly stemmed, and the secondary side pressure rises temporarily.

When the discharge operations are successively repeated, the above states (1) and (2) may be complicatedly combined depending on a discharge time and a discharge interval, and the pressure fluctuation may appear in such a manner that the state immediately before the discharge operation takes a pressure level higher or lower than the setting value contrary to the intent. This results in a problem of generating a difference between the intended discharge amount and the actual discharge amount.

The relief valve also has a similar problem caused by the pressure fluctuation when the valve is opened and closed with the setting pressure adjustment operation.

In view of the above-described situations, an object of the present invention is to provide a discharge device capable of suppressing pressure fluctuation of a compressed gas supplied to a container in which a liquid material is stored, and solving the problem of variation in discharge amount.

Solution to Problems

A liquid material discharge device according to the present invention comprises a storage container in which a liquid material is stored, a discharge port through which the liquid material is discharged, a pressure control valve that adjusts a pressure of a compressed gas supplied from an external compressed gas source to a desired level, a discharge valve that establishes or cuts off communication between the pressure control valve and the storage container, a control device that controls operation of the discharge valve, a first flow line connecting the pressure control valve and the discharge valve, and a second flow line connecting the discharge valve and the storage container, wherein the liquid discharge device further comprises a third flow line branched from the first flow line, and a leak mechanism connected to the third flow line, and the leak mechanism vents, to the outside, part of the compressed gas under the pressure adjusted by the pressure control valve.

In the above liquid material discharge device, the liquid material discharge device may be an air type dispenser.

In the above liquid material discharge device, the leak mechanism may include an orifice. The leak mechanism may include an orifice open-close mechanism that is constituted by connecting the orifice and an open-close valve disposed downstream or upstream of the orifice.

In the above liquid material discharge device including the orifice open-close mechanism, the open-close valve may be an automatic open-close valve that is opened and closed by the control device, and the control device may open and close the open-close valve in accordance with open-close condition information stored in advance. The leak mechanism may include the orifice open-close mechanism in plural sets connected in parallel. In that case, the plural sets of orifice open-close mechanisms preferably include a first orifice open-close mechanism, and a second orifice open-close mechanism providing a different flow rate from that provided by the first orifice open-close mechanism.

In the above liquid material discharge device, the leak mechanism may include a flow control valve providing a flow rate that is controllable by the control device.

In the above liquid material discharge device, the pressure control valve may be an electropneumatic regulator of which operation is controlled by the control device.

The above liquid material discharge device may further comprise a casing that contains the pressure control valve, the discharge valve, the leak mechanism, and the control device, the casing including a first joint to which a flow line in communication with the compressed gas source is detachably attached, and a second joint to which a flow line in communication with the discharge valve is detachably attached.

In the above liquid material discharge device, the leak mechanism may include a load-increasing vacuum mechanism connected to a terminal end of the third flow line.

The above liquid material discharge device may further comprise a vacuum mechanism for the discharge valve, the vacuum mechanism generating a negative pressure in a flow passage in the discharge valve.

The above liquid material discharge device may further comprise a buffer tank disposed in the first flow line.

An application device according to the present invention comprises the above liquid material discharge device, a worktable on which a workpiece is placed, a relatively moving device that moves the discharge port and the workpiece relative to each other, and a compressed gas source that supplies the compressed gas to the liquid material discharge device.

Advantageous Effects of Invention

According to the present invention, the problem of variation in discharge amount, attributable to the setting pressure adjustment operation of the pressure control valve, can be solved with the provision of the relief mechanism.

Furthermore, since the secondary side pressure of the pressure control valve is always kept lower than the setting pressure, stable discharge with smaller variation can be performed even in the case of a continuous discharge operation.

DESCRIPTION OF EMBODIMENTS

Embodiments for carrying out the present invention will be described below.

First Embodiment

Figure 1:
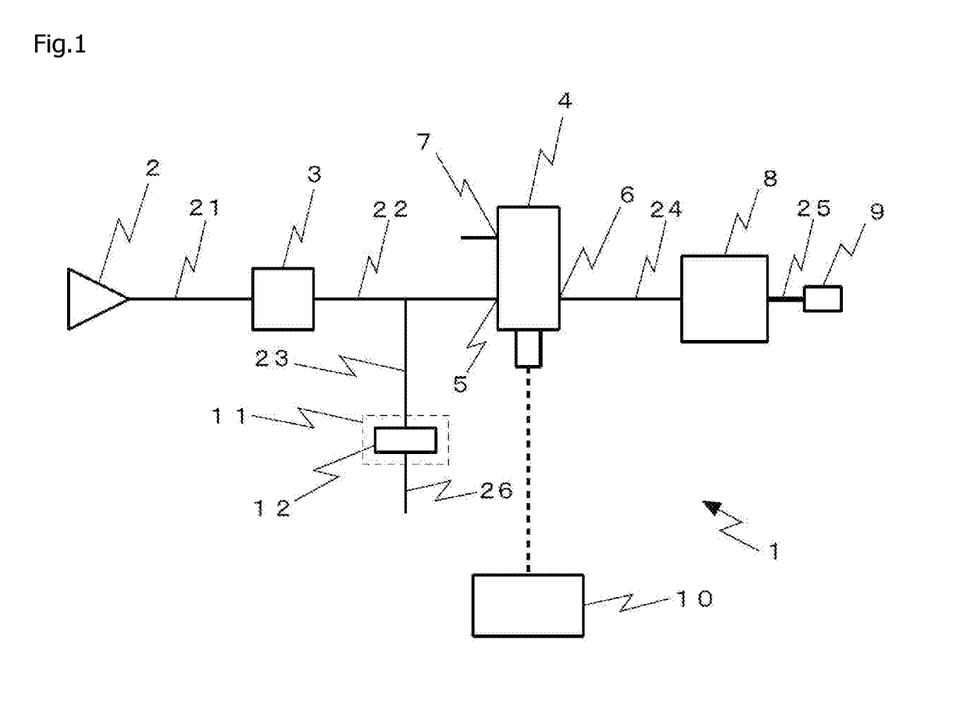
FIG. 1 is a block diagram referenced to explain a basic configuration of a discharge device according to a first embodiment.

FIG. 1 is a block diagram referenced to explain a basic configuration of a discharge device 1 according to a first embodiment.

The discharge device 1 according to the first embodiment includes a compressed gas supply source 2 that supplies a compressed gas, a pressure control valve (regulator) 3 that adjusts a pressure of the compressed gas supplied from the compressed gas source 2 to a desired level, a discharge valve 4 that establishes or cuts off communication between the pressure control valve 3 and a storage container 8 in which a liquid material is stored, a discharge port 9 through which the liquid material is discharged from the storage container 8 to the outside, a control device 10 that controls operation of the discharge valve 4, and a leak mechanism 11. Those components are arranged and connected in a layout illustrated in FIG. 1 through a plurality of flow lines 21 to 26. The discharge device is an air type dispenser for discharging the liquid material by the action of the compressed gas. In some cases, a plunger in the shape of a bomb shell is disposed to press the liquid material in a state where the plunger is held in close contact with an inner wall surface of the storage container 8.

The compressed gas source 2 is given by connecting a commercially-available compressed gas source in a replaceable manner. The compressed gas source 2 is constituted, for example, by a compressor for producing dry air, or a bomb filled with compressed air, nitrogen gas, or inert gas.

The pressure control valve 3 is constituted, for example, by a direct-acting solenoid valve for adjusting pressure with an adjustment screw or a pilot pressure, or by an electropneumatic regulator for adjusting pressure in accordance with the an externally-applied electrical signal. When the electropneumatic regulator is employed, its operation is preferably controlled by the control device 10.

The discharge valve 4 is a selector valve and is constituted, for example, by a solenoid valve changed over using an electromagnet, or by a pilot selector valve changed over in accordance with a pilot pressure. In this embodiment, a 3-port and 2-position selector valve is used to change over a position at which the pressure control valve 3 and the storage container 8 are communicated with each other, and a position at which the storage container 8 and the atmosphere are communicated with each other. However, the discharge valve 4 is not limited to that type selector valve, and it may be constituted by another type selector valve. Change-over operations of the discharge valve 4 are controlled by the control device 10.

After the pressure of the compressed gas supplied from the compressed gas source 2 has been adjusted to the desired level by the pressure control valve 3, the compressed gas is supplied to an inlet port 5 of the discharge valve 4. The flow line connected to the storage container 8 is connected to an outlet port 6 of the discharge valve 4. Thus, when the discharge valve 4 establishes communication between the inlet port 5 and the outlet port 6, the compressed gas supplied to the inlet port 5 is supplied to an upper space in the storage container 8. By the action of the compressed gas thus supplied, the liquid material stored in the storage container 8 is discharged to the outside through the discharge port 9. An amount of the liquid material discharged through the discharge port 9 can be adjusted by controlling, with the control device 10, a time length during which the communication between the inlet port 5 and the outlet port 6 is established by the discharge valve 4, the magnitude of the pressure adjusted by the pressure control valve 3, etc.

The storage container 8 is constituted by a commercially-available syringe.

A nozzle member including the discharge port 9 is communicated with the storage container 8 through the flow line 25. The discharge port 9 may be provided in the nozzle member that is directly connected to the storage container 8, without employing the flow line 25. Alternatively, the discharge port 9 may be provided in the storage container 8 itself.

The flow lines 21 to 26 may be constituted using hard members or flexible members (such as tubes).

The leak mechanism 11 in this embodiment is constituted by installing an orifice 12 in the middle of the flow line 23 that is branched from the flow line 22 connecting the pressure control valve 3 and the discharge valve 4. An end of the flow line 26 connected to the downstream side of the orifice 12 is opened to the atmosphere. Because part of the compressed gas of which pressure has been adjusted by the pressure control valve 3 is vent to the outside through the orifice 12, a substantive load capacity with respect to the pressure control valve 3 increases, whereby pressure fluctuation on the secondary side of the pressure control valve 3 (mainly in the storage container 8) can be reduced. Thus, the pressure fluctuation in the storage container 8 can be reduced, and variation in the amount of the liquid material discharged by the action of the compressed gas can be reduced.

Moreover, since part of the compressed gas passing through the flow line 22 is vent to the outside through the leak mechanism 11 (orifice 12 here), the pressure on the secondary side (downstream side) of the pressure control valve 3 is always kept lower than the setting value, and the pressure control valve 3 always performs an operation of raising the pressure (i.e., a supply operation). In other words, the pressure control valve 3 is avoided from performing a setting pressure adjustment operation in which the supply operation and a relief operation are repeated to realize the setting value. Accordingly, the state immediately before a discharge operation can be held constant, and stable discharge with smaller variation can be performed even in the case of a continuous discharge operation.

An amount of the compressed gas flowing to the outside through the orifice 12 depends on a diameter of the orifice 12. Preferably, the diameter of the orifice 12 is selected as appropriate corresponding to different values of the magnitude of the load capacity, a flow rate through the pressure control valve 3 (i.e., the secondary side pressure), etc. Whether the diameter is an appropriate size is determined, for example, on the basis of experiments conducted in advance. In this embodiment, the appropriate orifice size optimum for reducing the pressure fluctuation was checked by conducting the experiments in a manner of measuring pressure waveforms in the storage container 8 while actually changing the load capacity and the flow rate through the pressure control valve 3 (i.e., the secondary side pressure).

In more detail, the experiments were conducted on conditions of the size of the syringe, i.e., the storage container 8, ranging from 1 to 100 mL, the secondary side pressure (discharge pressure) of the pressure control valve set to 500 kPa at maximum, and the orifice diameter $\phi$ ranging from 0.1 to 2 mm. With the experiments, a good result was obtained, by way of example, in the case of the syringe size being 10 mL, the secondary side pressure (discharge pressure) of the pressure control valve being 100 kPa, and the orifice diameter $\phi$ being 0.4 mm. However, the above result is just one example. The orifice diameter is to be changed to another appropriate size depending on change of the syringe size, etc. Thus, for example, when the conditions such as the load capacity are changed and the orifice 12 has to be replaced, it is possible to smoothly replace the orifice 12 without conducting the experiments, etc. again, by previously obtaining a lot of data under various variations. Those data may be stored, as a table representing correlations between the load capacity and the orifice diameter, in a memory of the control device 10. Alternatively, an experimental formula derived on the basis of those data may be stored in the memory of the control device 10, and an optimum orifice diameter may be calculated dynamically. Other parameters than described above may be further referenced. For example, a vacuum pressure, a temperature of the compressed gas, a viscosity of the liquid material, etc. may also be referenced.

With the above-described discharge device 1 according to the first embodiment, variation in the discharge amount can be minimized by minimizing the pressure fluctuation attributable to the setting pressure adjustment operation of the pressure control valve 3 with the aid of the leak mechanism 11.

In addition, since the secondary side pressure of the pressure control valve 3 is always kept lower than the setting value by the leak mechanism 11, stable discharge with smaller variation can be performed even in the case of the continuous discharge operation.

Second Embodiment

Figure 2:
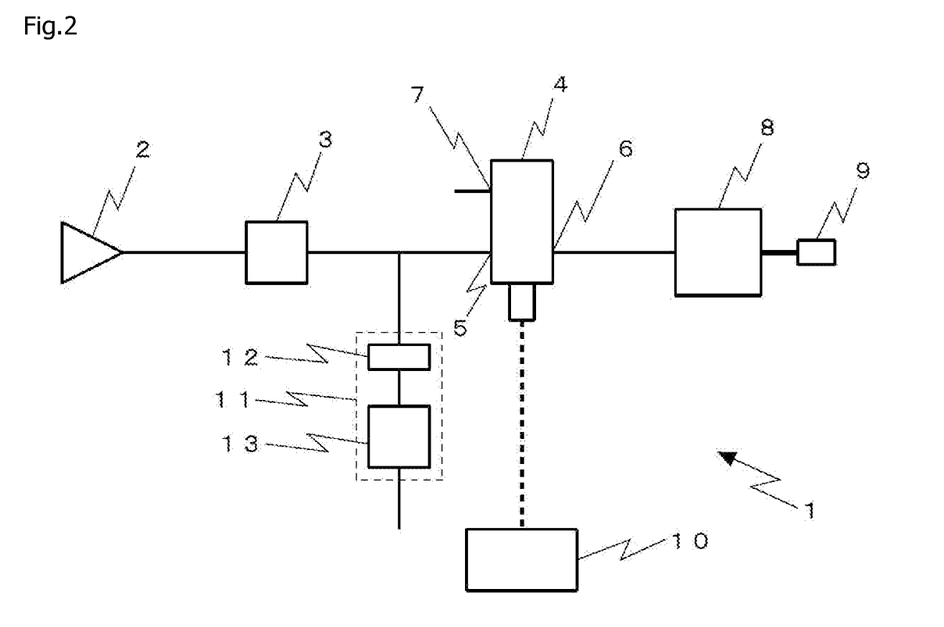
FIG. 2 is a block diagram referenced to explain a basic configuration of a discharge device according to a second embodiment.

FIG. 2 is a block diagram referenced to explain a basic configuration of a discharge device 1 according to a second embodiment. In the following, only different points from the configuration of the first embodiment (FIG. 1) are described, and description of the same points is omitted.

A leak mechanism 11 in the second embodiment is different from the leak mechanism 11 in the first embodiment in that an open-close valve 13 is disposed downstream of the orifice 12. The open-close valve 13 is effective when the pressure control valve 3 does not provide a sufficient flow rate relative to the load capacity.

When the pressure control valve 3 does not provide a sufficient flow rate relative to the load capacity, a long time is taken until the pressure of the compressed gas supplied to the storage container 8 reaches the setting value, after starting the operation of supplying the compressed gas to discharge the liquid material. In that case, the open-close valve 13 is operated to a "closed" state to stop the relief through the orifice 12. As a result, the time taken until the pressure of the compressed gas supplied to the storage container 8 reaches the setting value can be shortened.

On the other hand, when the pressure control valve 3 provides the sufficient flow rate relative to the load capacity (when the load capacity is reduced by replacing the storage container 8, for example), the open-close valve 13 is operated to an "open" state, thus causing part of the compressed gas to be always vented through the orifice 12. As a result, the pressure fluctuation attributable to the setting pressure adjustment operation of the pressure control valve 3 can be minimized.

The open-close valve 13 is just required to be changed over between two positions, i.e., "open" and "closed". The open-close valve 13 may be a manual open-close valve (e.g., a ball valve or a cock) that can be manually operated, or an automatic open-close valve (e.g., a solenoid valve or a pilot selector valve) that can be automatically operated in accordance with an electrical signal or a pilot pressure. When the automatic open-close valve is used, opening and closing operations are controlled by the control device 10.

Figure 9:
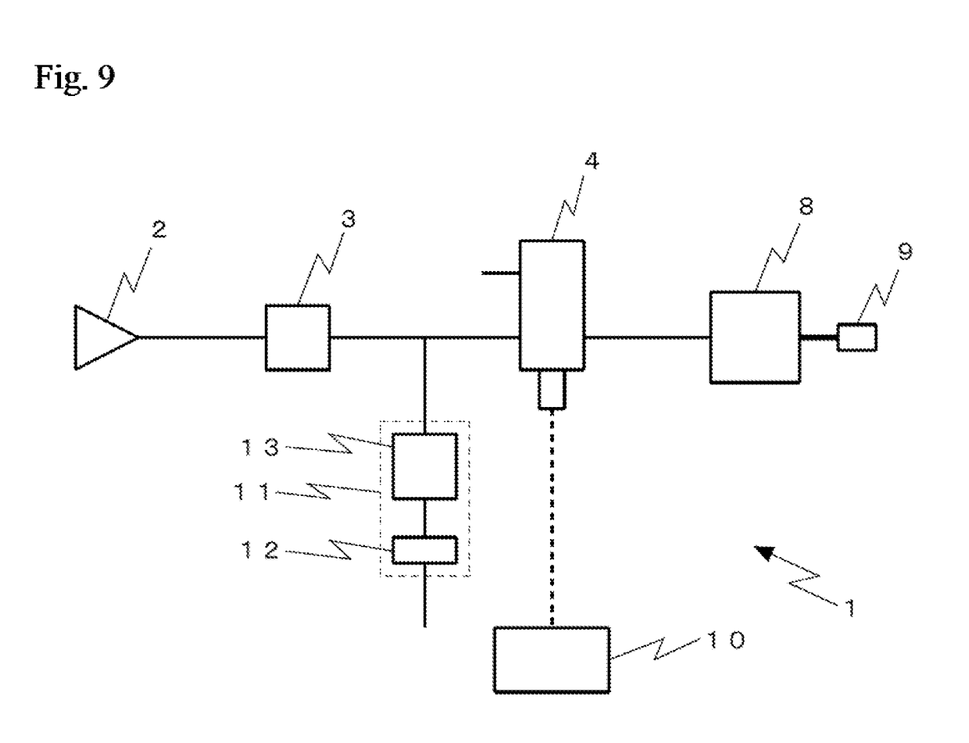
FIG. 9 is a block diagram referenced to explain a variation of the discharge device according to the second embodiment.

While FIG. 2 illustrates the case where the open-close valve 13 is arranged downstream of the orifice 12, the open-close valve 13 may be arranged upstream of the orifice 12 (see FIG. 9). However, when the open-close valve 13 is arranged upstream of the orifice 12, it is needed to take into account a relation between the resistance of the open-close valve 13 and the orifice diameter. Hence the open-close valve 13 is preferably arranged downstream of the orifice 12.

Whether the open-close valve 13 is operated to the "open" state or the "closed" state is preferably determined as follows. A boundary condition (like a threshold) between the "open" state and the "closed" state is determined by conducting experiments, which are similar to the above-described ones conducted in determining the diameter of the orifice 12, corresponding to different values of the magnitude of the load capacity, the flow rate through the pressure control valve 3 (i.e., the secondary side pressure), etc. The open-close valve 13 is then opened or closed on the basis of the boundary condition. For instance, the load capacity (such as the size of the storage container 8) at which the pressure fluctuation is minimized is sought by conducting the experiments in a manner of measuring pressure waveforms in the storage container 8 while actually changing the load capacity and the flow rate through the pressure control valve 3 (i.e., the secondary side pressure). A good result was obtained, by way of example, by operating the open-close valve 13 to the "opened" state when the syringe size was 10 mL, and the "closed" state when the syringe size was 20 mL, on condition of the secondary side pressure (discharge pressure) of the regulator, i.e., the pressure control valve, being set to 100 kPa. However, the above result is just one example. It is preferable to previously obtain a lot of data under various variations, and to store, in the memory of the control device 10, an open-close condition table representing conditions of operating the open-close valve to the "open" state or the "closed" state. As an alternative, preferably, an experimental formula derived on the basis of those data is stored in the memory of the control device 10, and optimum open-close conditions are calculated dynamically. Thus, the open-close valve 13 can be automatically operated to the "open" state or the "closed" state by the control device 10 depending on change of the load capacity (by inputting, for example, the pressure downstream of the pressure control valve, the flow rate through the pressure control valve, the flow rate through the orifice 12, and the load capacity of the storage container 8).

Preferably, a leak from the leak mechanism 11 during non-use of the discharge device 1 is made zero by holding the open-close valve 13 in the "closed" state when a power supply of the discharge device 1 is turned off. In the case of employing an automatic open-close valve as the open-close valve 13, the open-close valve 13 is preferably automatically operated to the "closed" state by the control device 10 when the power supply is turned off.

With the above-described discharge device 1 according to the second embodiment, change of the load capacity varying depending on the size of the storage container 8 and the lengths of the flow lines can be absorbed by the leak mechanism 11.

Third Embodiment

Figure 3:
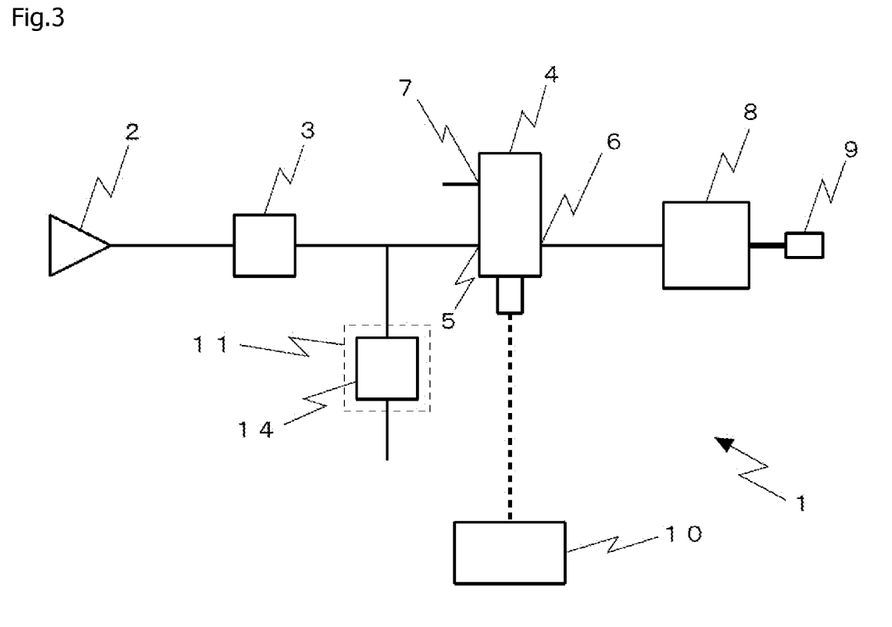
FIG. 3 is a block diagram referenced to explain a basic configuration of a discharge device according to a third embodiment.

FIG. 3 is a block diagram referenced to explain a basic configuration of a discharge device 1 according to a third embodiment. In the following, only different points from the configuration of the first embodiment (FIG. 1) are described, and description of the same points is omitted.

A leak mechanism 11 in the third embodiment is different from the leak mechanism 11 in the first embodiment in that a flow control valve 14 capable of changing a flow rate is disposed instead of the orifice 12.

In the third embodiment, even when the pressure control valve 3 and the storage container 8 need to be replaced with other types, the pressure fluctuation attributable to the setting pressure adjustment operation of the pressure control valve 3 can be minimized by adjusting the amount of the compressed gas to be released with the flow control valve 14. In the first embodiment (FIG. 1) including only the orifice 12, the orifice 12 needs to be replaced in some cases under similar situations.

The flow control valve 14 may be a needle valve or a servo valve, for example. Although the flow control valve 14 may be optionally of the manually or automatically operated type, its operation is preferably automatically controllable by the control device 10. The same state as that resulting from operating the open-close valve 13 of the leak mechanism 11 in the second embodiment to the "closed" state can be obtained by setting an opening degree of the flow control valve 14 to zero.

Preferably, a leak from the leak mechanism 11 during non-use of the discharge device 1 is made zero by holding the flow control valve 14 in the "closed" state when the power supply of the discharge device 1 is turned off. In the case of employing the flow control valve 14 that is automatically controllable, the flow control valve 14 is preferably automatically operated to the "closed" state by the control device 10 when the power supply is turned off.

With the above-described discharge device 1 according to the third embodiment, the leak mechanism 11 is able to dynamically absorb change of the load capacity varying depending on the size of the storage container 8 and the lengths of the flow lines, and to make the discharge device 1 adaptable for replacement of the pressure control valve 3.

Fourth Embodiment

Figure 4:
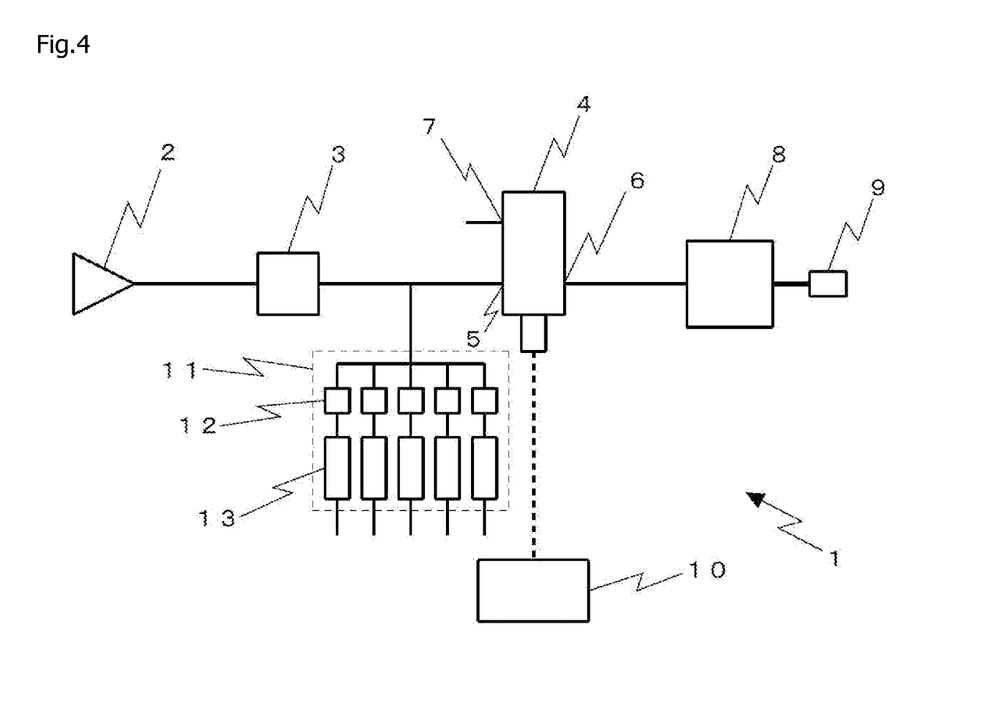
FIG. 4 is a block diagram referenced to explain a basic configuration of a discharge device according to a fourth embodiment.

FIG. 4 is a block diagram referenced to explain a basic configuration of a discharge device 1 according to a fourth embodiment. In the following, only different points from the configuration of the first embodiment (FIG. 1) are described, and description of the same points is omitted.

A leak mechanism 11 in the fourth embodiment includes a plurality of orifices 12, and open-close valves 13 in the same number as the orifices 12. In other words, it can be said that, in the fourth embodiment, the leak mechanism 11 in the second embodiment (FIG. 2) is disposed in plural numbers and arranged in parallel. While FIG. 4 illustrates an example in which five sets of the open-close valves 13 and the orifices 12 are disposed, the set number is not limited to five, and it may be four or less or six or more.

The orifices 12 are preferably constituted by orifices providing different flow rates (namely, having different diameters) from one another. This is because the discharge device is made adaptable for change of the load capacity by previously preparing the orifices 12 having different diameters, and operating selected one or more of the open-close valves 13 to the "open" state even when the pressure control valve 3 and the storage container 8 are replaced with other types. In the fourth embodiment, all the open-close valves 13 are preferably automatic open-close valves that can be automatically opened and closed by the control device 10.

Preferably, a leak from the leak mechanism 11 during non-use of the discharge device 1 is made zero by holding the open-close valves 13 in the "closed" state when the power supply of the discharge device 1 is turned off. In the case of employing the automatic open-close valves as the open-close valves 13, the open-close valves 13 are preferably automatically operated to the "closed" state by the control device 10 when the power supply is turned off.

With the above-described discharge device 1 according to the fourth embodiment, the leak mechanism 11 is able to dynamically absorb change of the load capacity varying depending on the size of the storage container 8 and the lengths of the flow lines, and to make the discharge device 1 adaptable for replacement of the pressure control valve 3.

Fifth Embodiment

Figure 5:
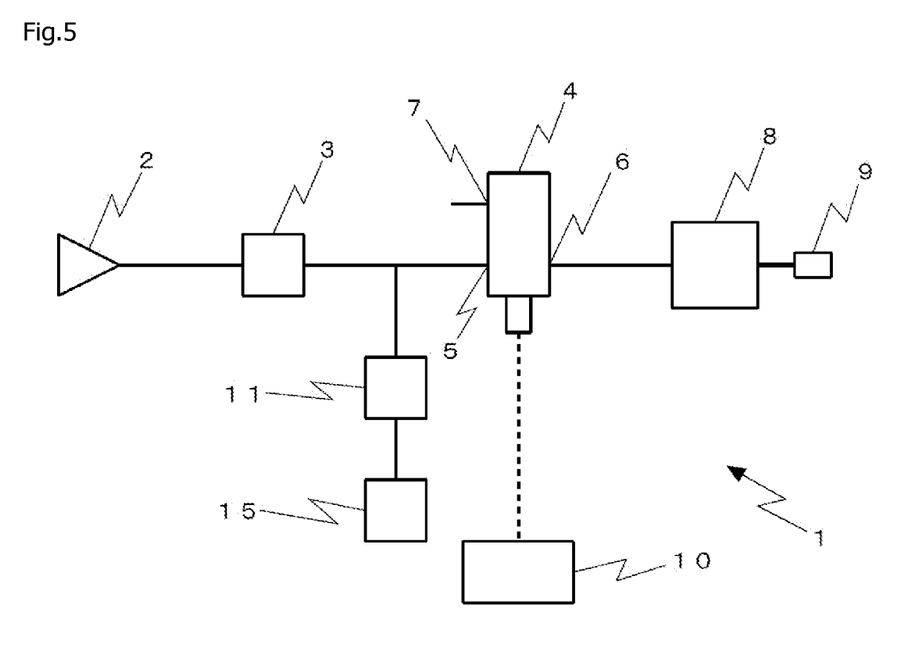
FIG. 5 is a block diagram referenced to explain a basic configuration of a discharge device according to a fifth embodiment.

FIG. 5 is a block diagram referenced to explain a basic configuration of a discharge device 1 according to a fifth embodiment. In the following, only different points from the configuration of the first embodiment (FIG. 1) are described, and description of the same points is omitted.

A leak mechanism 11 in the fifth embodiment is equipped with a vacuum mechanism 15 at its end, as illustrated in FIG. 5, instead of simply opening the end to the atmosphere. By connecting the vacuum mechanism 15, the load capacity can be increased in comparison with the case of opening the end to the atmosphere, and the effect of reducing the pressure fluctuation can be enhanced. For example, an ejector or a vacuum pump is used as the vacuum mechanism 15.

The vacuum mechanism 15 can be applied to the leak mechanism 11 in any of the first to fourth embodiments as well.

With the above-described discharge device 1 according to the fifth embodiment, a desired load capacity can be realized by increasing the load capacity with the vacuum mechanism 15.

Sixth Embodiment

Figure 6:
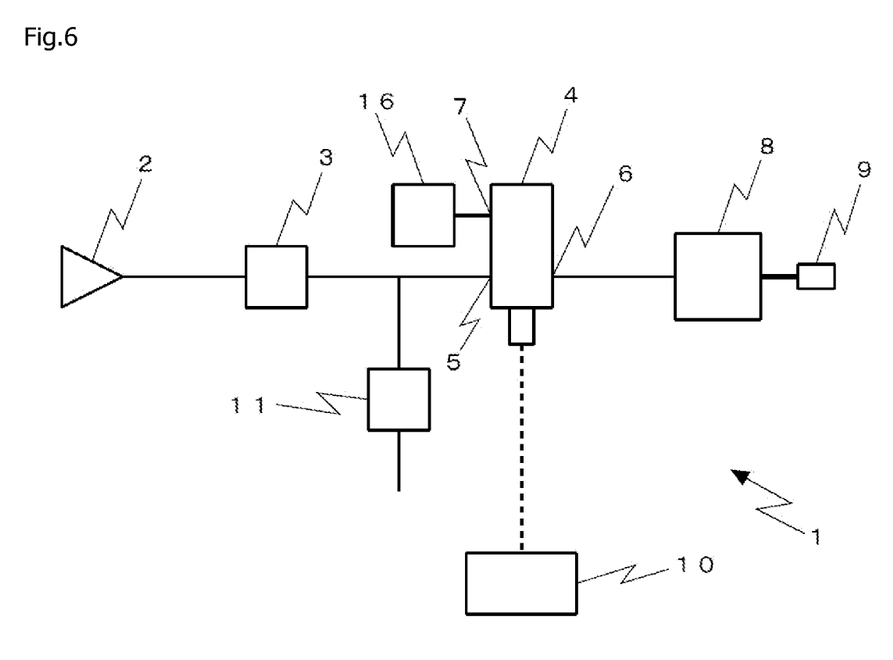
FIG. 6 is a block diagram referenced to explain a basic configuration of a discharge device according to a sixth embodiment.

FIG. 6 is a block diagram referenced to explain a basic configuration of a discharge device 1 according to a sixth embodiment. In the following, only different points from the configuration of the first embodiment (FIG. 1) are described, and description of the same points is omitted.

A discharge valve 4 in the sixth embodiment is equipped with a vacuum mechanism 16 connected to an exhaust port 7. The vacuum mechanism 16 can more promptly stop the liquid by applying a negative pressure to the storage container 8 at the end of the discharge, or can prevent dripping of the liquid by applying a negative pressure to the storage container 8 in a standby state. For example, an ejector or a vacuum pump is used as the vacuum mechanism 16.

Operations of the discharge valve 4 are similar to those in the first to fifth embodiments. (1) During a discharge operation, an inlet port 5 and an outlet port 6 are communicated with each other. (2) At the end of the discharge operation, the communication between the inlet port 5 and the outlet port 6 is cut off, and the outlet port 6 is communicated with the exhaust port 7 to vent, to the atmosphere, the compressed gas supplied to the storage container 8.

A leak mechanism 11 may be constituted as in any of the first to fifth embodiments.

With the above-described discharge device 1 according to the sixth embodiment, the liquid can be stopped more promptly and can be prevented from dripping with the aid of the vacuum mechanism 16. Even when the discharge device includes the vacuum mechanism 16, the pressure fluctuation on the secondary side of the pressure control valve 3 can be minimized, and stable discharge with smaller variation can be performed even in the case of the continuous discharge operation.

Seventh Embodiment

Figure 7:
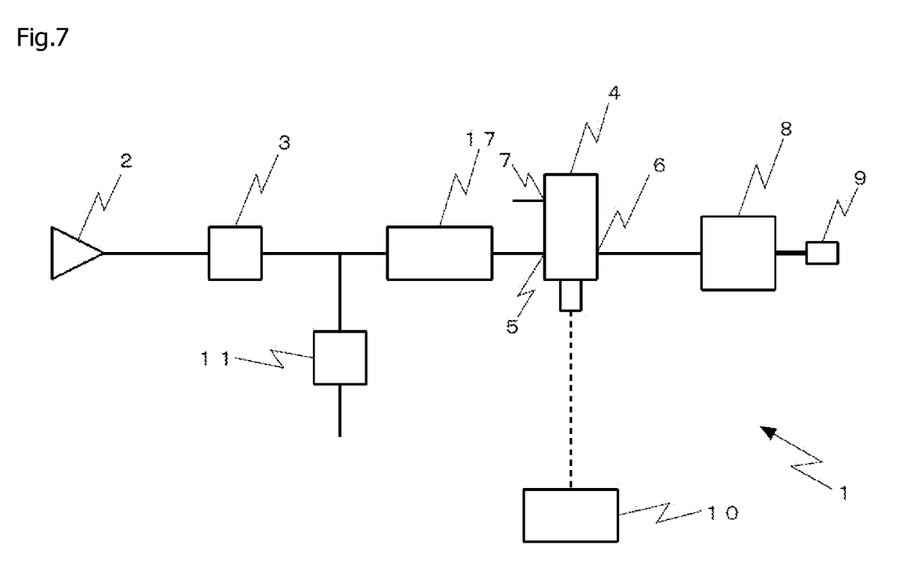
FIG. 7 is a block diagram referenced to explain a basic configuration of a discharge device according to a seventh embodiment.

FIG. 7 is a block diagram referenced to explain a basic configuration of a discharge device 1 according to a seventh embodiment. In the following, only different points from the configuration of the first embodiment (FIG. 1) are described, and description of the same points is omitted.

The discharge device 1 according to the seventh embodiment includes, as illustrated in FIG. 7, a buffer tank 17 between the pressure control valve 3 and the discharge valve 4. An internal volume of the buffer tank 17 is, for example, 1.5 to 100 times that of the storage container 8, and is preferably 1.5 times or more and less than 10 times from the viewpoint of a device size.

When the buffer tank 17 is disposed, the leak mechanism 11 is preferably branched from a point between the pressure control valve 3 and the buffer tank 17. In that case, a combined flow resistance of both the flow line upstream of the buffer tank 17 and the leak mechanism 11 is preferably set to be larger than that of the flow line downstream of the buffer tank 17. The discharge device 1 including the buffer tank 17 is described in detail in Japanese Patent No. 5460132 (Patent Document 3) patented to the applicant.

The leak mechanism 11 may be constituted as in any of the first to fifth embodiments.

With the above-described discharge device 1 according to the seventh embodiment, the buffer tank 17 makes it possible to steeply raise an internal pressure of the storage container 8, and to perform discharge operation at a higher pitch than in the discharge device not including the buffer tank. Also in the discharge device including the buffer tank 17, the pressure fluctuation on the secondary side of the pressure control valve 3 can be minimized with the aid of the leak mechanism 11, and stable discharge with smaller variation can be performed even in the case of the continuous discharge operation.

Eighth Embodiment

Figure 8:
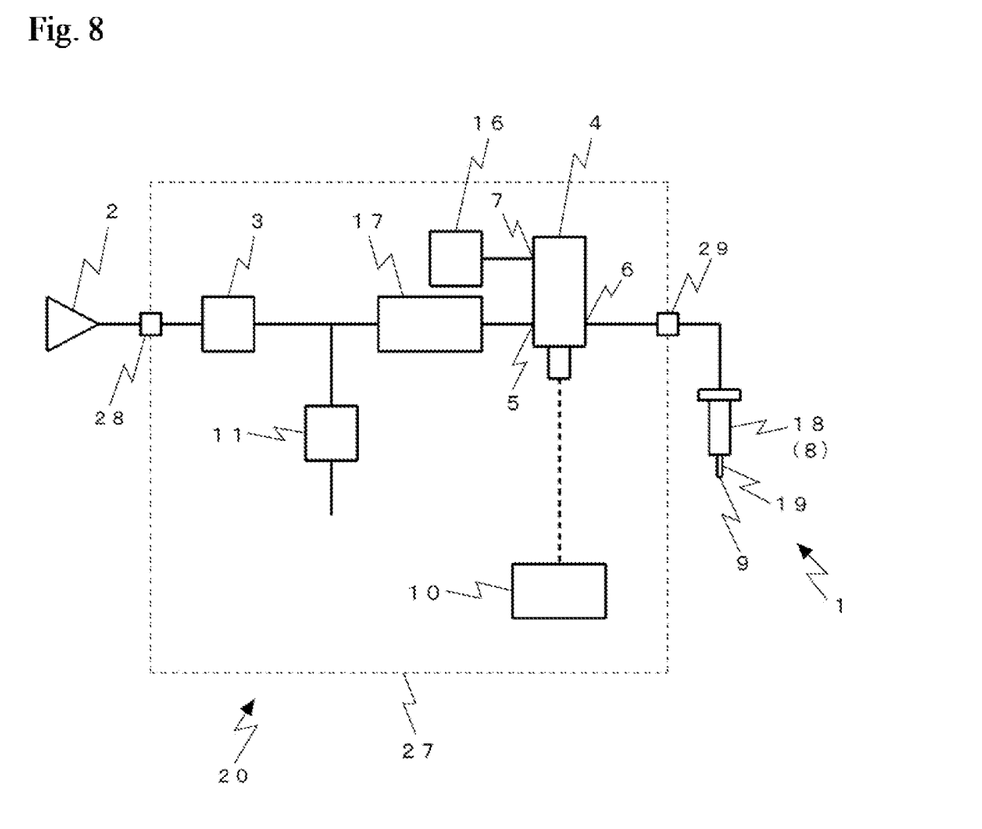
FIG. 8 is a block diagram referenced to explain a basic configuration of a discharge device according to an eighth embodiment.

FIG. 8 is a block diagram referenced to explain a basic configuration of a discharge device 1 according to an eighth embodiment. In the following, only different points from the configuration of the first embodiment (FIG. 1) are described, and description of the same points is omitted.

The discharge device 1 according to the eighth embodiment mainly includes a compressed gas source 2 that supplies a compressed gas, a dispense controller 20, a syringe 18 serving as a storage container 8 in which a liquid material is stored, and a nozzle 19 having a discharge port 9 through which the liquid material is discharged to the outside from the storage container 8.

The dispense controller 20 is constituted by a set of components installed in one casing 27, and includes a pressure control valve 3 that adjusts a pressure of the compressed gas supplied from the compressed gas source 2 to a desired level, a buffer tank 17 in which the compressed gas is stored, a discharge valve 4 that establishes or cuts off communication between the pressure control valve 3 and the syringe 18, a vacuum mechanism 16 that is connected to an exhaust port 7 of the discharge valve 4, and that is communicated with the syringe 18 at the end of the discharge operation to make a negative pressure act on the syringe 18, a control device 10 that controls operation of the discharge valve 4, and a leak mechanism 11 that vents, to the outside, part of the compressed gas of which pressure has been adjusted by the pressure control valve 3, those components being all arranged in the casing 27. In the casing 27 of the dispense controller 20, the individual components are arranged and connected through flow lines as illustrated in FIG. 8. Connection portions of the casing 27 to the compressed gas source 2 and the syringe 18 are each constituted to be detachable using joints 28, 29 or the like. Thus, handling of the discharge device, such as transportation and installation of the casing and replacement of the consumables, is facilitated by separately constituting the compressed gas source 2, which tends to become a large-sized unit, and the syringe 18 and the nozzle 19, which are frequently replaced as consumables, in the detachable form using joints 28, 29 or the likes.

After the pressure of the compressed gas supplied from the compressed gas source 2 has been adjusted to the desired level by the pressure control valve 3, the compressed gas is supplied to an inlet port 5 of the discharge valve 4. A flow line connected to the syringe 18 is connected to an outlet port 6 of the discharge valve 4. Thus, when the discharge valve 4 establishes communication between the inlet port 5 and the outlet port 6, the compressed gas supplied to the inlet port 5 is supplied to the syringe 18. By the action of the compressed gas thus supplied, the liquid material stored in the syringe 18 is discharged to the outside through the discharge port 9 of the nozzle 19. An amount of the liquid material discharged through the discharge port 9 can be adjusted by controlling a time length during which the communication between the inlet port 5 and the outlet port 6 is established through the discharge valve 4, the magnitude of the pressure adjusted by the pressure control valve 3, etc.

A leak mechanism 11 may be constituted as in any of the first to fifth embodiments.

The dispense controller 20 and the syringe 18 are connected to each other through a flexible tube. The syringe 18 may be held by an operator's hand or mounted to an application device equipped with an XYZ-axis drive device. The syringe 18 is moved relative to a worktable by the XYZ-axis drive device, and is used in work of applying the liquid material onto a workpiece. The XYZ-axis drive device is constituted, for example, as a known combination of an XYZ-axis servo motor and a ball screw.

Also in the discharge device 1 according to this embodiment, with the aid of the leak mechanism 11, the pressure fluctuation on the secondary side of the pressure control valve 3 can be minimized, and stable discharge with smaller variation can be performed even in the case of the continuous discharge operation.

LIST OF REFERENCE SIGNS

1: discharge device (as a whole), 2: compressed gas source, 3: pressure control valve (regulator), 4: discharge valve, 5: inlet port, 6: outlet port, 7: exhaust port, 8: storage container, 9: discharge port, 10: control device, 11: leak mechanism, 12: orifice, 13: open-close valve, 14: flow control valve, 15: a vacuum mechanism (for increasing load), 16: vacuum mechanism (for discharge valve), 17: buffer tank, 18: syringe, 19: nozzle, 20: dispense controller, 21 to 26: flow lines

The invention claimed is:

1. A liquid material discharge device comprising:
a storage container in which a liquid material is stored;
a discharge port through which the liquid material is discharged;
a pressure control valve that adjusts a pressure of a compressed gas supplied from an external compressed gas source to a setting value by raising and lowering the pressure of the compressed gas supplied from the external compressed gas source;
a discharge valve that establishes or cuts off communication between the pressure control valve and the storage container, the discharge valve comprising an inlet port, an outlet port and an exhaust port;
a controller that controls operation of the discharge valve such that during a discharge operation, the inlet port and the outlet port are communicated with each other, and at the end of the discharge operation, the communication between the inlet port and the outlet port is cut off, and the outlet port is communicated with the exhaust port to vent the compressed gas inside the storage container through the exhaust port;
a first flow line connecting the pressure control valve and the inlet port of the discharge valve, the pressure control valve supplies the compressed gas and the pressure of the compressed gas is adjusted in the first flow line between the pressure control valve and the discharge valve; and
a second flow line connecting the outlet port of the discharge valve and the storage container,
wherein the liquid material discharge device further comprises a third flow line branched from the first flow line upstream of the inlet port of the discharge valve and downstream of the pressure control valve, and a leak valve or a leak orifice provided on the third flow line,
the leak valve or the leak orifice is configured to leak a part of the compressed gas the pressure of which is adjusted by the pressure control valve so as to suppress pressure fluctuations in the second flow line and the storage container, and
during the discharge operation, the leak valve or leak orifice is configured to continuously leak an amount of the compressed gas which is supplied through the first flow line and the third flow line from the pressure control valve and which is necessary to keep the pressure of the compressed gas in the first flow line lower than the setting value such that the pressure control valve continues to perform a supply operation of the compressed gas during the discharge operation.

2. The liquid material discharge device according to claim 1, wherein a fixed amount of liquid material is discharged through the discharge port by supplying the compressed gas to the storage container.

3. The liquid material discharge device according to claim 1, wherein the leak valve or the leak orifice is constituted by one orifice.

4. The liquid material discharge device according to claim 3, further comprising an open-close valve disposed downstream or upstream of the one orifice, wherein the one orifice and the open-close valve constitute an orifice open-close mechanism.

5. The liquid material discharge device according to claim 4, wherein the open-close valve is an automatic open-close valve that is opened and closed by the controller.

6. The liquid material discharge device according to claim 4, wherein the liquid material discharge device includes the orifice open-close mechanism in plural sets connected in parallel.

7. The liquid material discharge device according to claim 6, wherein the plural sets of orifice open-close mechanisms include a first orifice open-close mechanism, and a second orifice open-close mechanism providing a different flow rate from that provided by the first orifice open-close mechanism.

8. The liquid material discharge device according to claim 1, wherein the leak valve or the leak orifice includes a flow control valve providing a flow rate that is controllable by the controller.

9. The liquid material discharge device according to claim 1, wherein the pressure control valve is an electropneumatic regulator of which operation is controlled by the controller.

10. The liquid material discharge device according to claim 1, further comprising a casing that contains the pressure control valve, the discharge valve, the leak valve or leak orifice, and the controller,
wherein the casing includes a first joint to which a flow line in communication with the compressed gas source is detachably attached, and a second joint to which a flow line in communication with the discharge valve is detachably attached.

11. The liquid material discharge device according to claim 1, further comprising a load-increasing vacuum connected to a terminal end of the third flow line.

12. The liquid material discharge device according to claim 1, further comprising a vacuum for the discharge valve, the vacuum generating a negative pressure in a flow passage in the discharge valve.

13. The liquid material discharge device according to claim 1, further comprising a buffer tank disposed in the first flow line.

14. An application device comprising the liquid material discharge device according to claim 1, a worktable on which a workpiece is placed, a moving device that moves the discharge port and the workpiece relative to each other, and the external compressed gas source that supplies the compressed gas to the liquid material discharge device.

* * * * *